(12) United States Patent
Smith

(10) Patent No.: US 9,222,880 B2
(45) Date of Patent: Dec. 29, 2015

(54) PROBE FOR DETECTING UNDERGROUND SUBSTANCES, AND METHOD

(71) Applicant: Sarcos LC, Salt Lake City, UT (US)

(72) Inventor: Fraser M. Smith, Salt Lake City, UT (US)

(73) Assignee: Sarcos LC, Salt Lake City, UT (US)

( * ) Notice: Subject to any disclaimer, the term of this patent is extended or adjusted under 35 U.S.C. 154(b) by 142 days.

(21) Appl. No.: 14/037,655

(22) Filed: Sep. 26, 2013

(65) Prior Publication Data

US 2015/0083901 A1 Mar. 26, 2015

(51) Int. Cl.
  *G01N 3/00* (2006.01)
  *G01N 21/27* (2006.01)
  *F41H 11/16* (2011.01)
  *G01N 21/85* (2006.01)

(52) U.S. Cl.
  CPC ............... *G01N 21/27* (2013.01); *F41H 11/16* (2013.01); *G01N 21/8507* (2013.01)

(58) Field of Classification Search
  CPC ..... G01N 21/27; G01N 21/84; G01N 33/227; G01N 33/24
  USPC ................................ 73/84, 85; 250/226, 269.1
  See application file for complete search history.

(56) References Cited

U.S. PATENT DOCUMENTS

| | | | | |
|---|---|---|---|---|
| 5,461,229 A * | 10/1995 | Sauter et al. | .................. | 250/253 |
| 5,591,902 A * | 1/1997 | Castagner | ......................... | 73/84 |
| 5,739,536 A * | 4/1998 | Bucholtz et al. | ............ | 250/341.2 |
| 7,628,059 B1 * | 12/2009 | Scherbring | ....................... | 73/84 |

* cited by examiner

*Primary Examiner* — Thanh Luu

(57) ABSTRACT

A probe for underground sensing of materials of interest, for example chemicals such as explosives, includes a probe body that is capable of being inserted into the ground, and one or more sensors that are able to sense one or more materials in the vicinity of at least a portion of the probe body. The sensor(s) may include a light source that directs light to the vicinity of the portion of the probe body, and a light detector, such as a photosensor or spectrometer, that detects reflected light from the material around the probe body. The reflected light may be analyzed to determine the presence of one or more materials of interest, such as chemicals used in explosive devices. The probe may be part of a vehicle used to detect and neutralize buried explosive devices, with the probe for example being on an articulable arm of the vehicle.

18 Claims, 3 Drawing Sheets

PROBE FOR DETECTING UNDERGROUND SUBSTANCES, AND METHOD

GOVERNMENT RIGHTS

This invention was made with United States Government Support under Contract Number FA8650-11-C-7187 with the United States Air Force. The United States Government has certain rights in this invention.

FIELD OF THE INVENTION

The invention is in the field of detection and analysis of underground substances.

DESCRIPTION OF THE RELATED ART

The current approach to handling possible buried improvised explosive devices (IEDs), for example devices detected in roads, is to dig up the possible IED, preferably using a vehicle with a specialized digging arm that allows the vehicle to dig up the possible IED at a distance from the occupied portion of the vehicle. The device is then exploded using a separate explosive charge. This is a time-consuming and laborious process.

SUMMARY OF THE INVENTION

A probe that is capable of being inserted into the ground, such as by being drive into the ground, senses surrounding materials in situ, using at least one light source and at least one light detector, with data gathered by the at least one light detector being used to determine composition information regarding the surrounding materials.

According to an aspect of the invention, a probe that includes: a probe body that is capable of being driven or otherwise inserted into the ground; and a sensor that senses one or more chemicals in underground material around a portion of the probe body.

According to an aspect of the invention, a method of underground sensing, the method includes the steps of: inserting a probe into the grounds; and sensing, using a sensor of the probe, one or more materials in the ground around the probe.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

The annexed drawings, which are not necessarily to scale, show various aspects of the invention.

DETAILED DESCRIPTION

A probe for underground sensing of materials of interest, for example chemicals such as explosives, includes a probe body that is capable of being driven or otherwise inserted into the ground, and one or more sensors that are able to sense one or more materials in the vicinity of at least a portion of the probe body. The sensor(s) may include a light source that directs light to the vicinity of the portion of the probe body, and a light detector, such as a photosensor or spectrometer, that detects reflected light from the material around the probe body. The reflected light may be analyzed to determine the presence of one or more materials of interest, such as chemicals used in explosive devices. The probe may be part of a vehicle used to detect and neutralize buried explosive devices, with the probe for example being on an articulable arm of the vehicle. The sensor may substantially continuously monitor surrounding materials while the probe is being driven or otherwise inserted into the ground, with changes in readings being used as a guide for when the probe has been inserted into the right location, for example to analyze an object of interest that was detected earlier. In this way, it can be confirmed that, an object that has been detected some approximate distance below the surface, has been penetrated, and contains substances that are not like the surrounding ground material. The probe and the hole made by the insertion of the probe may be used in detonation of the object while the object is still buried, perhaps with a detonation charge being pushed into place in the hole by the probe.

Figure 1:
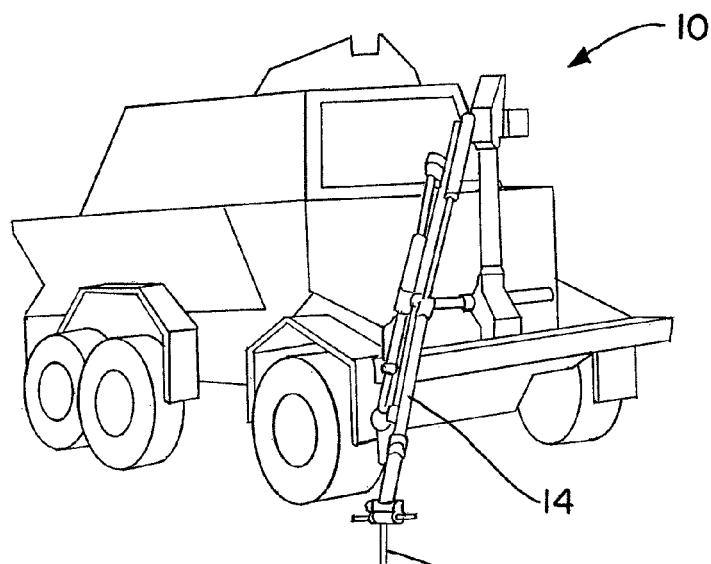
FIG. 1 is a perspective view of a vehicle, according to an embodiment of the present invention.

FIG. 1 shows a vehicle 10 that is used to find buried explosive devices, such as improvised explosive devices (IEDs). The vehicle 10 has a probe 12 that can be inserted into the ground to examine a suspicious object that has been found. The suspicious object, such as a possible IED, may have been detected prior to the examination by the probe 12, for example by vehicle-mounted ground-penetrating radar, which may be mounted on a separate vehicle, or alternatively may be part of the vehicle 10. The suspicious object may also have been detected in any of a variety of other ways.

The probe 12 is on the end of an articulable and/or extendible arm 14 of the vehicle 10. The arm 14 may allow positioning of the probe 12, while maintaining the main part of the vehicle 10 (where the operator is located) at a significant distance away from the probe 12, for example at a distance of at least 6 m (20 feet) away from the probe 12. The arm 14 may include one or more additional tools, for example a component that allows an operator to dig out a device of interest, a component that allows an operator to blow up a device while it is still underground, and/or a camera or other imaging device.

The arm 14 may include a device for pushing, hammering, or pushing and hammering, the probe 12 into the ground, or for otherwise driving the probe 12 into the ground. The hammering device may use electrical forces, hydraulic forces, pneumatic forces, or other suitable forces.

Figure 2:
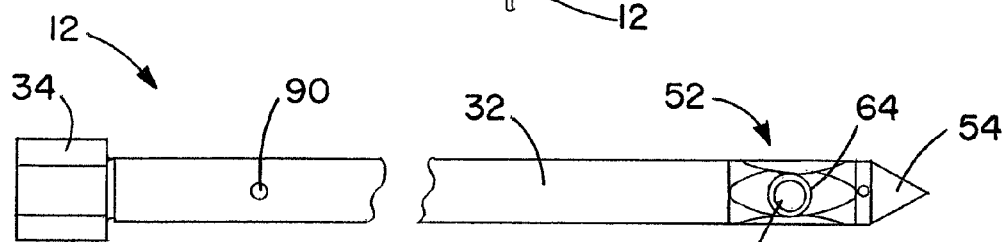
FIG. 2 is a side view of a probe that is part of the vehicle of FIG. 1.
Figure 3:
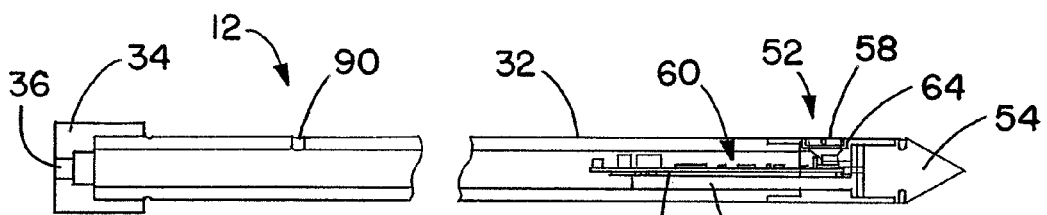
FIG. 3 is a side sectional view of the probe of FIG. 2.
Figure 4:
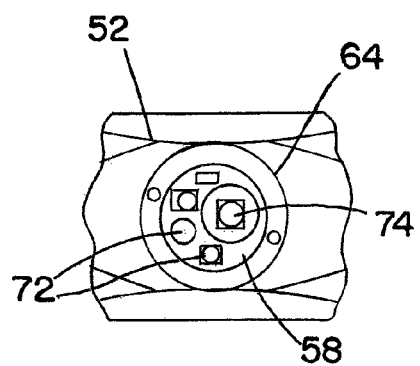
FIG. 4 is a magnified view of a sensor section that is part of the probe of FIG. 2.

FIGS. 2-4 show further details regarding the probe 12. The probe 12 includes a cylindrical main probe body 32 that runs most of the length of the probe 12. In one embodiment the probe 12 has a length of at least 1 m, such as a length of 1.1 m (42 inches), although many other lengths are possible. At one end of the main probe body 32 is a head 34 that is used for pushing or hammering the probe 12 into the ground. The head 34 includes an opening 36 for receiving an actuator or hammer adapter to link the head 34 to an actuator or hammer, such as a pneumatic actuator or hammer, for pushing or hammering (driving) the probe 12 into the ground. The probe body 32 and the head 34 may be made of steel or another suitable material.

At the opposite end of the probe body 32 is a sensor section 52, and a pointed tip 54 that is coupled to the sensor section 52. The main probe body 32, the head 34, the sensor section 52, and the tip 54 may all be considered as parts of a probe body. The tip 54 is the part of the probe 12 that initially makes contact with the ground, and may be made of a hardened or wear-resistant material, for example tool steel. The sensor section 52 includes an optical window 58 that is used passing light between a sensor assembly 60 that is in the hollow interior of the probe body 32 and the sensor section 52, and material adjacent to and just outside of the window 58. The window 58 may be made of a suitable optically-transmissive material, for example sapphire or fused quartz. An O-ring 64 seals the opening for the sensor section 52, preventing materials from outside the probe 12 from getting into the hollow interior of the probe body 32 and the sensor section 52.

The sensor assembly 60 includes one or more light sources 72, one or more light detectors 74, electronics 76, and a mounting plate 78. The light source(s) 72 emit through the window 58 light of specific wavelengths or ranges of wavelengths, for illumination of outside material around the probe 12, such as earth or underground material that the sensor section 52 is located in. The light sources 72 may emit light in ultraviolet (UV) through near-infrared (near-IR) spectrum. Light emitting diodes (LEDs) may be used as the light sources 72, since LEDs have the advantage of providing repeatable and precise light outputs. Alternatively the light sources 72 may be other types of light sources, emitting light at single wavelengths or bands of wavelengths.

In an embodiment, the sensor assembly 60 includes six LEDs as the light sources 72, emitting light of wavelengths of interest, for example wavelengths that would disclose the presence of chemicals or materials that may be included in IEDs, such as one or more of ammonium nitrate, aluminum, fuel oil, calcium ammonium nitrate, potassium chlorate, flour, and sugar. More or fewer light sources 72 may be employed.

The light detector(s) 74 may be photodetectors and/or spectrometers that receive light, and perhaps characterize the incoming signals by light wavelength and intensity. The one or more light detectors 74 may detect in wavelengths of interest, wavelengths and associated intensities corresponding to materials of interest, such as the chemicals or materials listed in the previous paragraph.

The light sources 72 and/or the light detectors 74 may be operatively coupled to the electronics 76. The electronics 76 may be used to control the sources 72 and/or the detectors 74, to interpret data received by the light detectors 74, and/or to communicate data and/or materials detected by the sensor system. The electronics 76 may be on or embodied as a circuit board or other such device, which may be mounted on the mounting plate 78, which in turn may be attached or connected to the probe body 32, the sensor section 52, and/or the tip 54.

The electronics 76 may be used to identify materials in the vicinity of the light detectors 74. Different materials emit different intensities of characteristic wavelengths of light when illuminated by the light sources 72. The electronics 76 may compare the light intensities of various wavelengths that are received by light detectors 74 with signatures for materials of interest, such as the various explosive materials listed above. The signatures may be expressed in any of a variety of ways, such as relative and/or absolute light intensities at various wavelengths. A catalog of material signatures, such as a look-up table, may be compiled for a given sensor assembly configuration, for example by exposing the sensor to various materials (placing the sensor section 52, or the operative parts of it) in proximity to various materials, and cataloging the resulting output of the light detectors 74. One or more algorithms may be used to determine what material is present outside of the window 58. For example a ratio of reflectance amplitudes at a given pair of light wavelengths (e.g., 830 nm and 275 nm) may be used to distinguish between dirt and one or more explosive materials. As another example, raw amplitudes of reflected light at a single wavelength (or combinations of wavelengths) may be used to differentiate between materials of interest. The electronics 76 also may be able to identify various non-explosive materials that are likely to be encountered, for example sand or various other types of dirt (including earth at various levels of moisture).

Connections from the sensor assembly 60 to outside of the probe 12 may run through a hole or opening 90 in the probe body 32. The connections may provide power to the sensor assembly 60, and may transport data received by or produced by the sensor assembly 60. The connections may be made using one or more cables or other suitable devices. Alternatively data to and from the sensor assembly 60 may be transmitted wirelessly, and power can be supplied by on board batteries.

The sensor assembly 60 may provide output to an operator of the vehicle 10 regarding what material is in proximity to the window 58. The output may be in terms of whether the material is dirt, is an explosive, or is some unidentified material. Specific explosive materials may be identified to the operator. The output may be provided in any of a variety of suitable ways, including visual and/or audio signals. Visual output may be in terms of text and/or a variety of visual indicators, such as different colored lights (e.g., green for dirt, red for an explosive, and yellow for an unidentified material).

Some or all of the analysis of the sensor assembly 60, such as the identification of different materials, may alternatively be performed outside of the probe 12. Further, it may be possible to locate the one or more light sources 72, the one or more light detectors 74, and/or the electronics 76 outside of the main probe body or at the upper end of the probe body. For instance, fiber optic cables may be used to route light from external light sources, or the upper portion of the probe body, to the window 58, and light received at the window 58 to one or more external light detectors, or to one or more light detectors located in the upper portion of the probe body.

The sensor assembly 60 may be configured to allow data for additional materials to be input and stored. For example, when a material encountered that is unidentified, identification may later be obtained in other ways, such as by excavating the material and perhaps chemically testing it. This information may be input into and stored in the electronics 76, to allow identification of similar material in the future.

Figure 5:
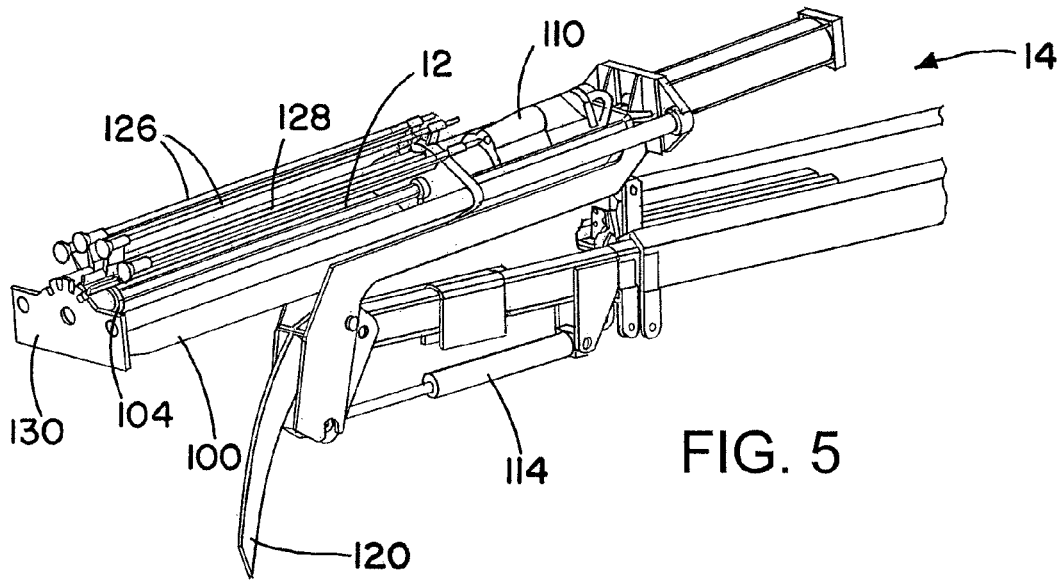
FIG. 5 is an oblique view of a portion of the arm of the vehicle of FIG. 1, showing a frame that houses the probe of FIG. 2, with the frame in a first position.
Figure 6:
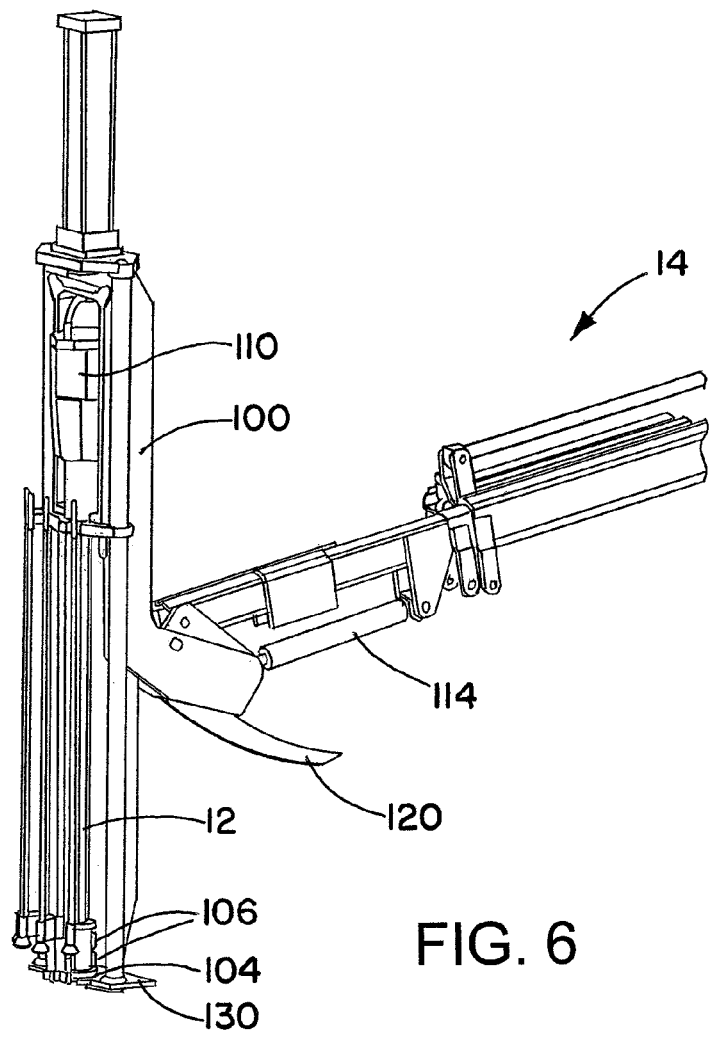
FIG. 6 is another oblique view of the arm portion of FIG. 5, with the frame in a second position.
Figure 7:
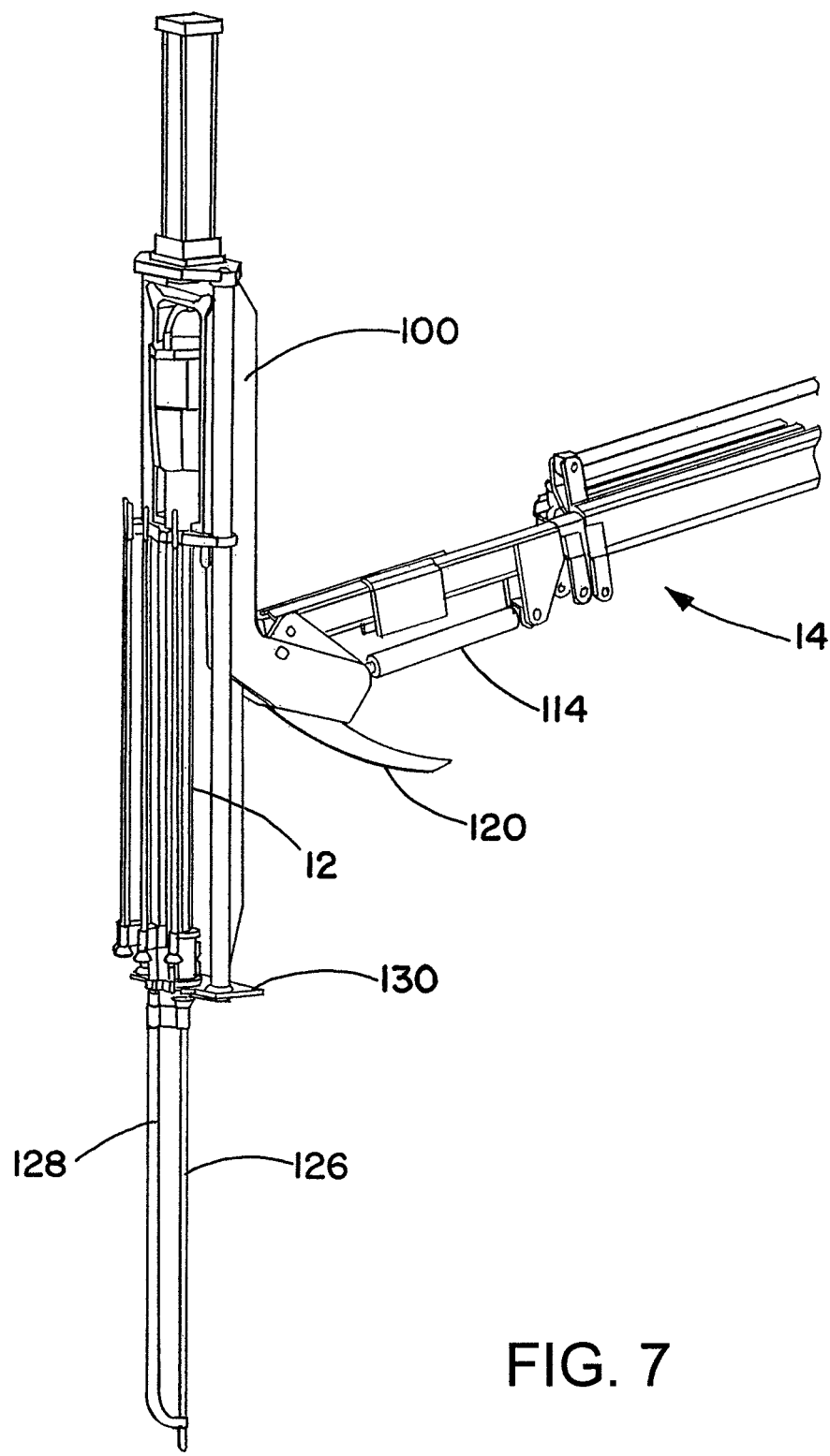
FIG. 7 is yet another view of the arm portion of FIG. 5, illustrating deployment of a detonator.

FIGS. 5-7 show a mounting for the probe 12, for deployment of the probe 12 and other components from the end of the vehicle arm 14. The probe 12 is in a frame 100 that provides alignment of the probe 12 during insertion and extraction. The frame 100 may include a brush wiper 104 to clean the window 58 (FIG. 4), as the probe 12 is inserted into and/or extracted from the ground. The frame 100 may also include a sensor calibration device 106, for example one or more probe reflectance calibration discs, used to calibrate parts of the sensor assembly 60 (FIG. 3), such as the one or more light sources 72 (FIG. 4) and/or the one or more light detectors 74 (FIG. 4).

A pneumatic hammer 110 is also located within the frame 100. The pneumatic hammer 110 is used for driving the probe 12 into the ground, and for extracting the probe 12 from the ground. The hammer 110 is only one example of an actuator that may be used to insert the probe 12 into the ground. One alternative is an actuator that applied a steady or slowly-varying pressure force alone to push the probe 12 into the ground, without using an impact force. Another alternative is a combination or pressure and impact. A further alternative would be to use rotation, such as by use of a motor, either on its own, or in conjunction with other insertion mechanisms. For example, alternatively the probe 12 may be equipped with flutes or other drill-like features on the outside either (i) at the front, (ii) at the front plus partially up the length, or (iii) at the front plus down the full length of the probe 12, to actively pull the probe into the ground with each rotation. Or the probe 12 may be inserted using rotation without any flutes or other drill features. An advantage of the rotational method is that it substantially reduces the shock loading to the probe 12 (as compared to the impact hammer assisted methods), which may be advantageous in preserving the integrity of the probe 12.

A hydraulic actuator 114 is used to pivot the frame 100 and a spike 120, to allow either the spike 120 or the tools on the frame 100 to be employed. The spike 120 may be used to dig into soil, and/or to dislodge a partially or fully buried device. FIG. 5 shows the arm 14 configured for use of the spike 120, and FIG. 6 shows the arm 14 configured for use of the probe 12 (or other tools on the frame 100).

As noted above, the arm 14 may be configured to detonate an object examined by the probe 12, using the hole that was made by the probe 12. Toward that end, the frame 100 may have mounted on it a series of detonators 126, which may have a diameter slightly less than that of the part of the probe 12 that is inserted into the ground. The detonators 126 may include detonators of different lengths, allowing different detonators to be selected for different depths in the ground. The detonators 126 are supported by a series of detonator supports 128. The detonator supports 128 can be individually moved to put an individual of the detonators 126 in a position, shown in FIG. 7, where the detonator 126 can be pushed by the free end of the probe 12 (the end with the tip 54 (FIG. 2) into a hole previously made by the probe 12. The movement of the detonator 126 may involve rotating the detonator 126 and the detonator support 128 about a bottom plate 130 of the frame 100, for example using a suitable actuator. During insertion the detonator 126 may be separated from its breakaway support 128. After the detonator 126 is inserted into the hole, and the probe 12 is again withdrawn, the vehicle 10 may be moved away, and the detonator activated to detonate the underground object.

The sensor assembly 60 may take data substantially continuously, for example at a rate of 300 Hz, or more broadly at at least 50 to 100 Hz. The data rate is of greatest importance during insertion of the sensor assembly. The rate of insertion used with these data rates may be 12.7 to 17.8 cm per second (5 to 7 inches per second), for example. Slower data acquisition rates may be used in conjunction with slower insertion rates. Multiple light sources may strobe in sequence, allowing measurement of the response of the material to light of different wavelengths of light.

Data acquisition may be performed during insertion of the probe 12, and may aid in positioning of the probe 12. For example the readings from the probe 12 during insertion may be used to determine when to stop inserting the probe 12 (when the sensor window 58 is positioned so as to no longer be detecting dirt). This use of data acquisition during insertion thus may be used as a feedback mechanism. Also, acquisition of readings during insertion of the probe 12 may be used as a confirmation of whether the probe location was correct. Often readings from ground-penetrating radar do not provide precise enough location information for an underground object to be located on the first insertion of the probe 12. Therefore it is advantageous to be able to quickly insert and extract the probe 12 multiple times at slightly different locations, being able to acquire data at a high rate all throughout the insertion process. For example, the probe 12 may have an insertable length about or within an order of magnitude of 1 meter (about 40 inches), and may be fully inserted in about or within an order of magnitude of 10 to 20 seconds after insertion is commenced.

An alternative way of controlling the insertion of the probe 12 is to place a load cell or force sensor at the top of the probe head 34. The load cell or force sensor may be used to sense changes in load needed to drive the probe 12 into the ground. These changes may be associated with changes in the material encountered by the probe. For example, an explosive material may provide a different resistance to insertion than earth around a buried device.

The probe 12 has been described above as being used for sensing explosives or other suspicious underground devices or substances. The probe 12 may also be useable to detect other sorts of material in the ground, whether or not as part of a device.

Analyzing a suspicious object in place allows operations to be greatly speeded up. Suspicious objects that are not dangerous (not made of explosive materials) may be identified and bypassed, without a need to excavate such objects or otherwise remove them. And by detonating dangerous or potentially dangerous underground objects in place, the removal of IEDs is made faster and more efficient.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:
1. A probe comprising:
   a probe body that is capable of being inserted into the ground; and
   a sensor that senses one or more chemicals in underground material around a portion of the probe body;
   wherein the probe is part of an articulable arm that is part of a vehicle; and wherein the arm includes detonators in operative combination with the probe, wherein the probe may be used to push one of the detonators into a hole left by extraction of the probe from the ground.

2. The probe of claim 1, wherein the sensor includes:
one or more light sources that illuminate the material around the portion of the probe body;
and one or more light detectors that receive light from the material around the portion of the probe body.

3. The probe of claim 2, wherein the one or more light sources include one or more light emitting diodes.

4. The probe of claim 2, wherein the one or more light detectors includes one or more spectrometers.

5. The probe of claim 2, wherein the probe body includes a window that passes light therethrough from the one or more light sources, and that passes reflected light to the one or more light detectors.

6. The probe of claim 5, wherein the window is located on a side surface of the probe body.

7. The probe of claim 2, wherein the sensor includes electronics that are operatively coupled to the electronics that analyze data from the one or more light detectors to determine composition of the underground material from reflections of light from the one or more light sources, received by the one or more light detectors.

8. The probe of claim 7, wherein the electronics analyzes the data from the one or more light detectors to determine if the underground material contains an explosive.

9. The probe of claim 7, wherein the electronics analyzes the data by comparing light spectra received by the one or more light detectors with stored values corresponding to materials of interest.

10. The probe of claim 9, wherein the materials of interest include one or more of ammonium nitrate, aluminum, fuel oil, calcium ammonium nitrate, potassium chlorate, flour, and sugar.

11. The probe of claim 1, in combination with an actuator on the arm to drive the probe into the ground.

12. The probe of claim 1, wherein the detonators include detonators of different length.

13. A method of underground sensing using the probe of claim 1, the method comprising:
inserting the probe into the ground; and
sensing, using the sensor of the probe, one or more materials in the ground around the probe.

14. The method of claim 13, wherein the sensing includes sensing one or more materials that are components of an explosive material.

15. The method of claim 13, wherein the inserting includes at least one of pushing, hammering, or rotating the probe.

16. The method of claim 13, wherein the sensing includes emitting light from one or more light sources of the probe, and detecting reflected light with one or more light detectors of the probe.

17. The method of claim 13, wherein the sensing includes sensing at a rate of at least 50 Hz, during the inserting.

18. The method of claim 17, wherein the results from the sensing during the inserting are used as feedback to control the inserting.

* * * * *